(12) United States Patent
Weston

(10) Patent No.: US 8,043,255 B2
(45) Date of Patent: Oct. 25, 2011

(54) CHAIR POWERED BREAST PUMP APPARATUS

(76) Inventor: Richard S. Weston, Encinitas, CA (US)

( * ) Notice: Subject to any disclaimer, the term of this patent is extended or adjusted under 35 U.S.C. 154(b) by 0 days.

(21) Appl. No.: 12/634,680

(22) Filed: Dec. 9, 2009

(65) Prior Publication Data

US 2010/0152652 A1 Jun. 17, 2010

Related U.S. Application Data

(60) Provisional application No. 61/201,365, filed on Dec. 9, 2008.

(51) Int. Cl.
*A61M 1/06* (2006.01)
*A47C 7/62* (2006.01)
(52) U.S. Cl. .................................... 604/74; 297/217.1
(58) Field of Classification Search .............. 297/180.16, 297/217.1, 180.1; 604/74, 152; 126/204; 417/230
See application file for complete search history.

(56) References Cited

U.S. PATENT DOCUMENTS

| | | | |
|---|---|---|---|
| 580,284 A * | 4/1897 | Krieg | 297/180.16 |
| 5,007,899 A | 4/1991 | Larsson | |
| 5,514,166 A | 5/1996 | Silver et al. | |
| 6,652,484 B1 | 11/2003 | Hunckler et al. | |
| 2005/0154349 A1 * | 7/2005 | Renz et al. | 604/74 |
| 2008/0045887 A1 | 2/2008 | Larsson et al. | |

OTHER PUBLICATIONS

International Search Report and Written Opinion issued May 6, 2010 for PCT/US2009/067404, 12 pages.

\* cited by examiner

*Primary Examiner* — Nicholas D Lucchesi
*Assistant Examiner* — Brooke Matney
(74) *Attorney, Agent, or Firm* — Eleanor M. Musick; Procopio, Cory, Hargreaves & Savitch LLP

(57) ABSTRACT

A chair powered breast pump apparatus has at least one breast shield adapted to fit over a nipple of a breast, a pump having a stationary portion and a reciprocating portion engaged for reciprocating movement, one or more suction lines connected in series between the stationary portion and the breast shield, a first connecting bracket configured to secure the reciprocating portion to a first portion of a chair movement mechanism, and a second connecting bracket configured to secure the stationary portion to a second portion of a chair movement mechanism, the first and second portions being relatively movable, whereby movement of the chair by a user seated in the chair reciprocates the reciprocating portion in and out of the stationary portion so as to apply suction to the breast shield.

33 Claims, 4 Drawing Sheets

CHAIR POWERED BREAST PUMP APPARATUS

RELATED APPLICATIONS

The present application claims the benefit of co-pending U.S. provisional patent application No. 61/201,365, filed on Dec. 9, 2008, the contents of which are incorporated herein by reference in their entirety.

BACKGROUND OF THE INVENTION

1. Field of the Invention

The present invention relates to breast pumps designed for extracting breast milk from a mother into a container for storage and infant feeding purposes.

2. Related Art

Working mothers often use breast pumps to extract milk from their breasts into a bottle for later feeding of their infant while the mother is at work or separated from the infant for some other reason. Current breast pump designs include a suction cup or breast shield for engagement over the breast and a pumping device connected to the breast shield, with a connector for attaching a container to the breast pump outlet to receive the milk. Manual breast pumps of various designs have existed for many years. These designs are not particularly efficient since they require use of small muscle groups of the arms and hands, and mothers using manual pumps of these designs generally tire easily, often before sufficient milk is collected. In general, the easier a pump is for the mother to operate, the more milk will be collected.

Some automated breast pumps have been devised in the past in which an electric motor or other power source drives a piston or diaphragm to operate the pump. U.S. Pat. No. 5,007,899 of Larsson, the contents of which are incorporated herein by reference, describes a drive unit adapted for use with a manual piston breast pump. The drive unit has an adaptor for releasably securing the cylinder of the breast pump to the unit, and a clamp on a drive arm of the unit is releasably secured to the breast pump piston. A motor in the unit drives the drive arm back and forth to reciprocate the piston at a desired suction stroke.

SUMMARY OF THE INVENTION

Embodiments described herein provide for a breast pump apparatus in which the pumping action is produced by movement of a chair or seat, such as a glider rocking chair, swinging office chair, swinging ottoman, recliner or the like.

According to one embodiment, a chair powered breast pump apparatus is provided, which comprises at least one breast shield adapted to fit over a nipple of a breast, a suction line having a first end coupled to the breast shield, a pump communicating with a second end of the suction line and a compressable pump component received for reciprocating movement relative to a stationary pump component between extended and retracted positions, a first connecting bracket configured to secure the compressable pump component to a first portion of a chair movement mechanism, and a second connecting bracket or adapter configured to secure the stationary pump component to a second portion of a chair movement mechanism, the portions being relatively movable. For example, one portion of the chair movement mechanism may be fixed to a stationary part of the chair or to a swivel and the other portion may be fixed to a moving or gliding part of the chair. Appropriate reciprocating pumps include a piston pump, a diaphragm pump or a bellows pump, among others.

In one embodiment, the chair is a rocking chair with a glider linkage mechanism mounting a seat, back rest, and arm rests of the chair on a fixed base or swivel base. The linkage mechanism may comprise a rectangular frame having a first pair of side rails secured to the fixed base, a second pair of side rails secured to opposite sides of the moving part of the chair, and front and rear pairs of links or levers pivotally connecting the fixed side rails to the moving side rails. In one embodiment, the cylinder is secured to one of the first pair of side rails on a first side of the mechanism, and the piston is secured to one of the second pair of side rails on the first side. Alternatively, the piston may be secured to a moving side rail while the cylinder is secured to a corresponding fixed side rail. In either case, rocking movement of the chair by a mother seated in the chair causes the piston to reciprocate back and forth in the cylinder and apply suction to the suction line. The chair powered breast pump apparatus may alternatively be configured to use with other chair configurations such as a rocker or a reclining chair by connecting the pump between two relatively movable portions of the chair.

In another embodiment, dual breast pumps may be used, with a first reciprocating pump secured to one side of the glider-type chair movement mechanism and a second reciprocating pump secured to the other side of the chair movement mechanism. The two suction lines may be connected to a manifold having suction ports for connection to two breast shields. The user may choose to connect a single shield to one of the ports and cap the other port, so that the single shield is connected to both pumps for more suction, or may connect the ports to first and second breast shields so that milk can be pumped from both breasts simultaneously.

In one embodiment, a control panel is mounted at a suitable location on the chair, for example on a chair arm, and includes the manifold with suction ports for connection to one or both breast shields, a switch to engage one or both pumps, and a regulator to adjust suction to a desired comfort level.

By incorporating a breast pump apparatus in the movement mechanism of a swinging glider type of chair, pumping of breast milk is made much easier for the mother, who can power such a chair easily by use of the larger muscle groups of the abdominals, thighs, and buttocks. These muscles do not tire as quickly as the hand and arm muscles used in manual breast pumping.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a chair operated pump apparatus in which the pump which provides suction for the apparatus is mounted between relatively moving parts of a chair movement mechanism of a recliner, glider or rocking type of chair.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
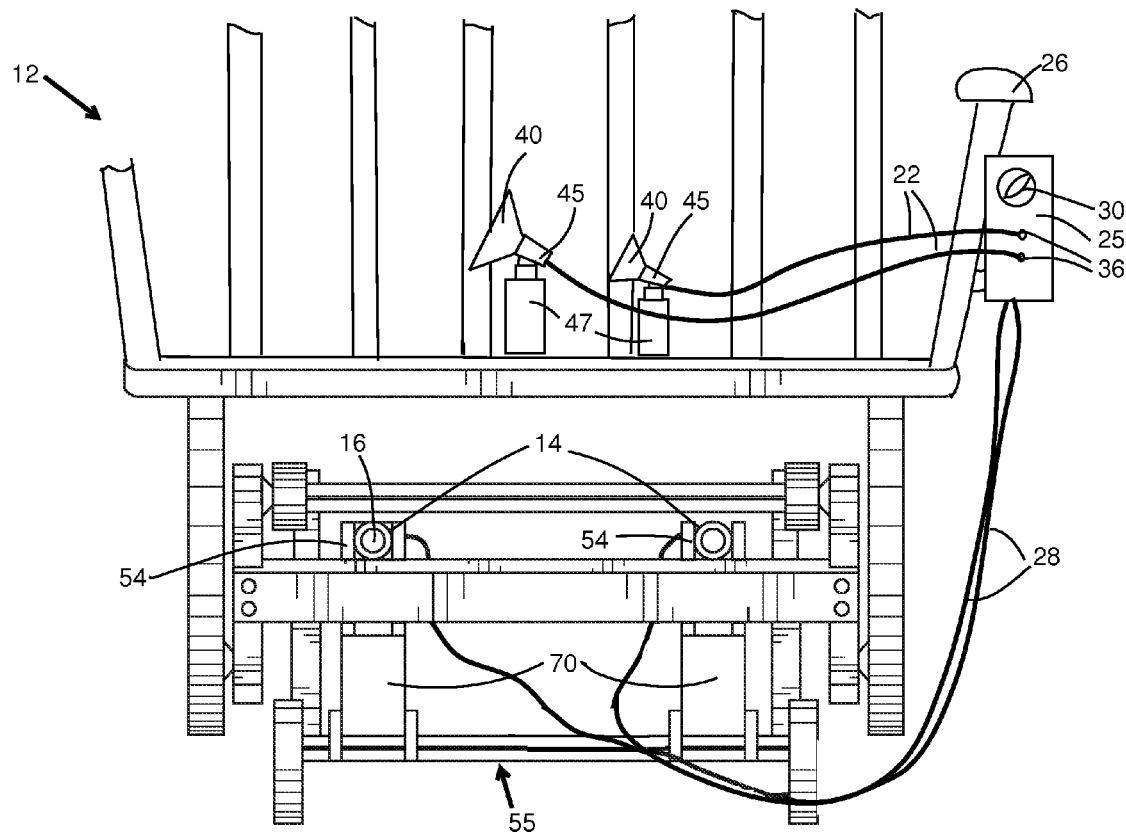
FIG. 1 is a front view of the lower portion of an exemplary glider type of chair incorporating a breast pump apparatus.
Figure 2:
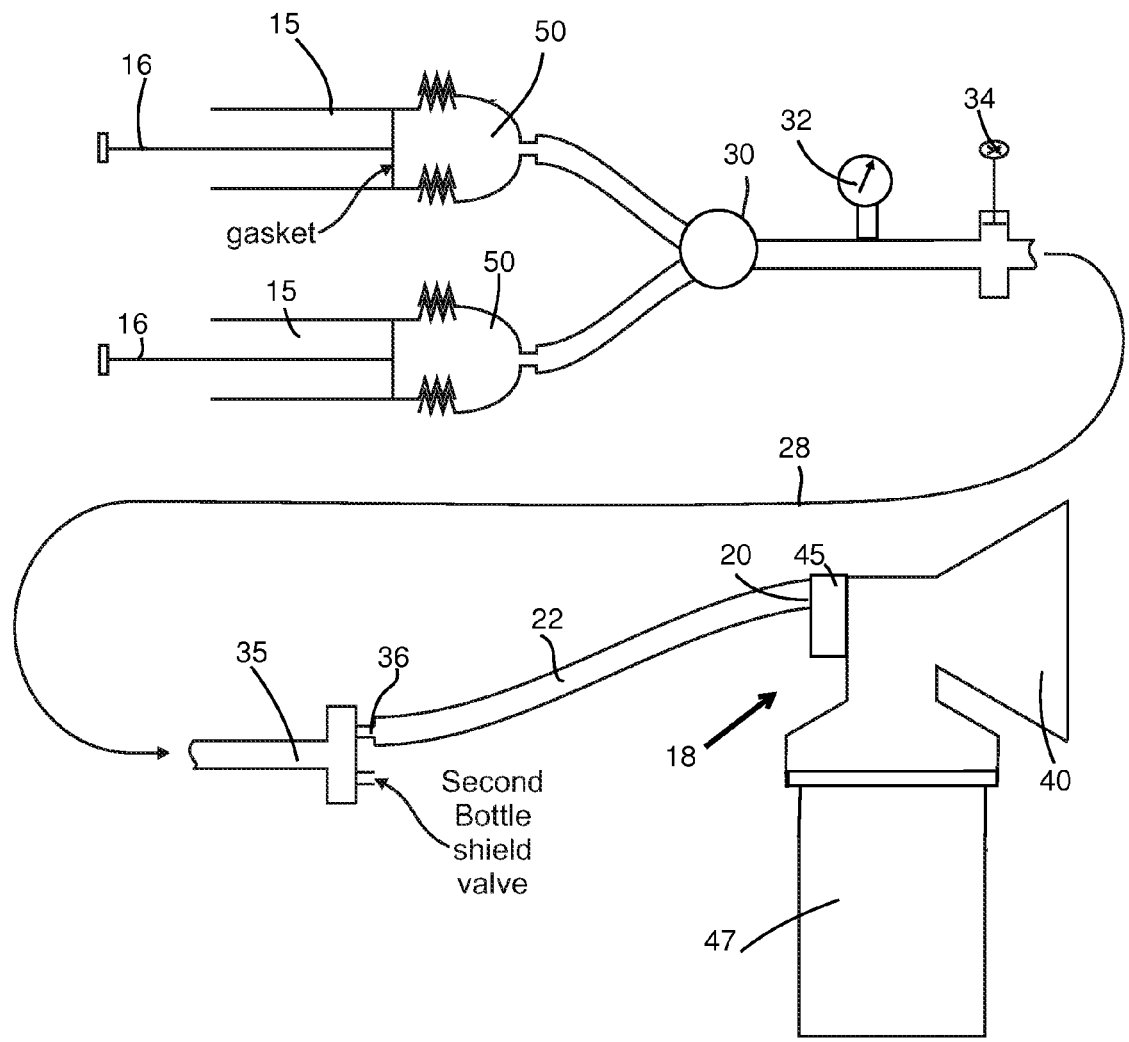
FIG. 2 is a diagrammatic view of one embodiment of a breast pump apparatus configured for incorporation in the chair of FIG. 1.

FIGS. 1 to 4 illustrate one embodiment of a breast pump apparatus 10 incorporated in a movable seat or user support. In the illustrated embodiment, the user support is a glider type of rocking chair 12, but the apparatus may be incorporated in other types of movable user supports or seats in other embodiments, such as office chairs, ottomans, reclining chairs, hammocks, swinging chairs, or the like. The basic apparatus 10 may be similar to a manually operated breast pump such as the manual breast pump assembly described in U.S. Pat. No. 5,007,899, the contents of which are incorporated herein by reference. As best illustrated in FIG. 2, apparatus 10 basically comprises one or more reciprocating pumps 14, which in the exemplary embodiment each comprise a cylinder 15 and a piston 16 reciprocally mounted in the cylinder, and one or more breast shield assemblies 18 connected to the cylinder 15. As will be readily apparent to those of skill in the art, the piston pump may be replaced by a diaphragm pump, a bellows pump, or similar pumps capable of providing the controlled vacuum that is required for extraction of breast milk. In one embodiment, each breast shield assembly has a suction port 20 connected to the cylinder 15 via a connecting passageway which comprises a first suction line 22, a connecting manifold 24 which may be incorporated in a control panel 25 at a suitable location on the chair 12, such as on an arm 26 of the chair as illustrated in FIG. 1, and a second suction line 28 which connects the cylinder 15 to the connecting manifold 24. The control panel 25 can alternatively be mounted within or attached to a hinged table or tray that can be moved into position after the mother is seated by flipping or pivoting the tray up or down. Such a tray or table would provide the added convenience of having a flat surface to place cleaning pads, tissues, extra bottles or other items that are useful during milk extraction within easy reach of the mother.

In the embodiment illustrated in FIG. 2, the apparatus has two second suction lines 28 which connect the manifold to two separate pumps 14, but additional pumps may be included to provide more suction if desired. The connecting manifold 24 includes a multiple unit switch 30 which allows a mother to switch between two or more pumps or suction units, a gauge 32 which allows a mother to monitor breast pumping pressure, a vacuum regulator 34, a filter 35, and a pair of suction ports 36 which may be selectively capped when not in use. As illustrated in FIGS. 1 and 2, two breast shield assemblies 18 may be secured to the respective suction ports 36, if desired. Alternatively, one breast shield assembly may be secured to one of the ports while the other port is capped.

The breast shield assembly 18 may be similar or identical to that described in U.S. Pat. No. 5,007,899 referenced above, to which reference is made for a detailed description of the construction of assembly 18. As illustrated in FIGS. 1 and 2, each breast shield assembly has a cone or funnel-shaped end 40 for fitting over a nipple, a cylindrical extension 42 which communicates with a collecting chamber (not visible in the drawings), and a suction port 20 for connection to suction line 22. A milk container or bottle 47 is releasably secured to an outlet of collecting chamber as indicated, and a valve member controls release of milk into container 47 at the end of a suction stroke when the vacuum is released. Reference is made to U.S. Pat. No. 5,007,899 for a description of the operation of breast shield assembly when connected to suction or piston pump 14.

The cylinder 15 of the exemplary piston pump has a threaded end for selective connection to the threaded outer portion 43 of suction outlet of the breast shield assembly or to an adaptor 50 (see FIGS. 3 and 4) which is designed to secure the cylinder to a first portion of a chair movement mechanism, as described in more detail below in connection with FIGS. 1, 3 and 4. The piston or piston rod 16 has a necked down portion 52 adjacent its outer end, as best seen in FIG. 4, which is received in a generally U-shaped clamp member or bracket 54. Bracket 54 may be secured to a second portion of the chair movement mechanism with a suitable fastener such as a screw or the like. The first and second portions move relative to one another as the chair movement is actuated by the user. Thus, the piston and cylinder move relative to one another as the chair is rocked or moved back and forth, reciprocating the piston relative to the cylinder so as to provide the desired pumping action, as described in more detail below in connection with FIGS. 3 and 4.

Figure 3:
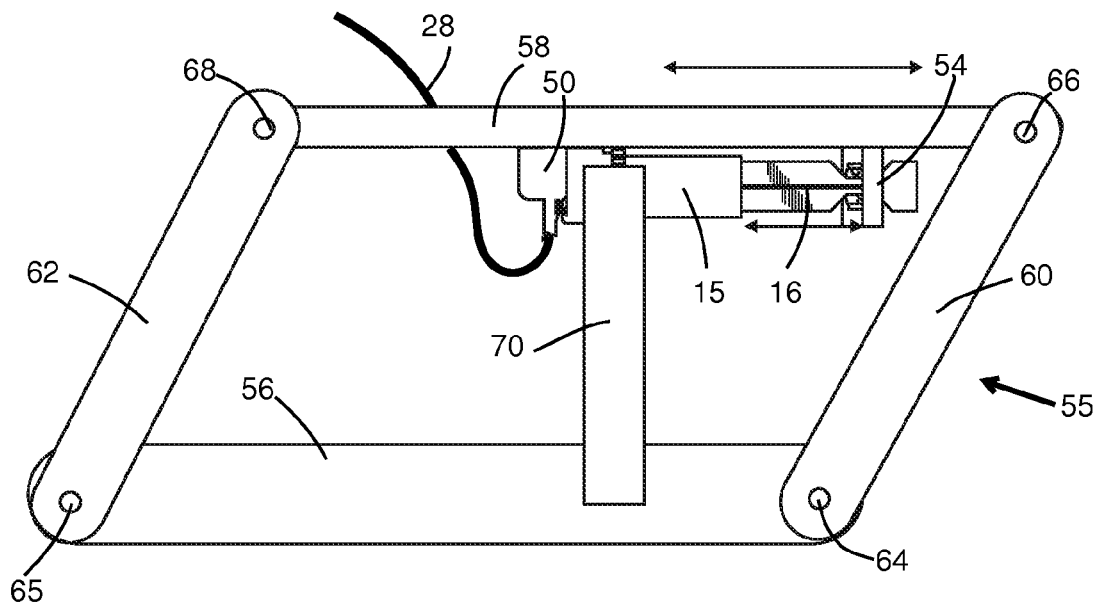
FIG. 3 is a side elevation view of the glider mechanism of the chair of FIG. 1 with the pump of the apparatus of FIG. 2 attached between relatively movable portions of the chair.
Figure 4:
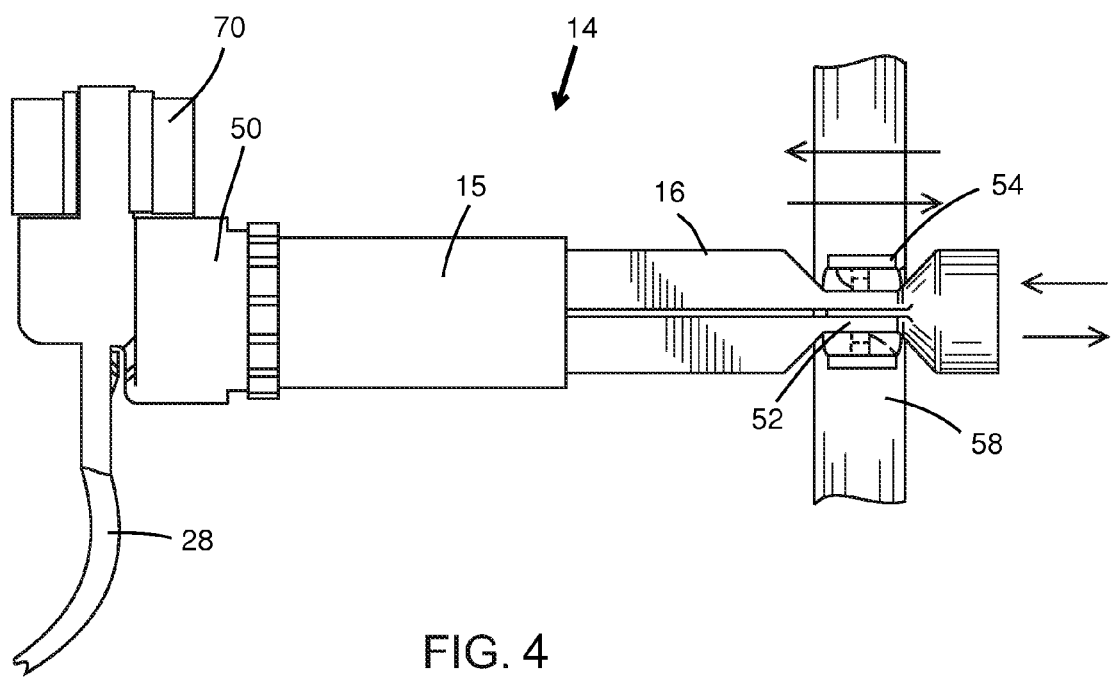
FIG. 4 is a top plan view of the pump of FIG. 3.

FIGS. 1, 3 and 4 illustrate one embodiment of the pump 14 secured to first and second portions of a glide rocker linkage mechanism 55 of the type used in many rocking chairs. As illustrated in the simplified view of FIG. 3, the mechanism 55 basically comprises a generally rectangular rocker frame having a base portion 56 secured to a stationary part of the chair or to a swivel for rotation of the chair and a seat or glide portion 58 secured to the body of the chair, and a pair of swivel links or levers 60, 62 each pivoted at one end to the base portion via pivots 64, 65 respectively and at the opposite end to seat portion 58 via pivots 66, 68, respectively. As illustrated in FIG. 3, the cylinder 15 is secured by connecting post or bracket 70 to the base portion of the chair rocker or glide mechanism, while the clamp member or bracket 54 is secured to the glide portion 58 via a screw fastener or the like. The bracket 54 may be releasably secured to the glide portion 58 so that it can be removed to allow the cylinder to be pulled out of adaptor 50 for cleaning, maintenance or replacement.

FIG. 3 illustrates the piston or piston rod 15 in an extended position at the end of a suction stroke. When the glide portion 58 pivots back to the left of the position shown, the piston is pushed back into the cylinder. As the glide portion 58 reverses direction and pivots back to the position shown in FIG. 3, the piston is pulled back outwards to the extended position in the suction stroke, applying suction to the breast shield 40 via suction lines 28 and 22 and pumping milk into chamber 44. In the reverse stroke, valve 48 opens and milk is dispensed into container 47. Thus, suction is created in a cyclic pattern with suction evacuated via a suitable evacuation hole in the cylinder at the end of each stroke.

As indicated in FIG. 2, two or more pumps 14 may be secured to the suction ports 36 via respective suction lines 28, so as to provide more suction to a single breast shield (with the second suction port capped) or to provide suction to two breast shields for pumping milk from both breasts simultaneously. The user can readily control the amount of suction by use of the controls on control panel 25, which may be conveniently mounted on an arm of the chair in a readily accessible position. The single/double switch 30 on the control panel may be used by the mother to control the number of pumps which are active, and thus the amount of suction available. Thus, the user or mother can engage one pump or move the switch to a different position to engage two, three, or more pumps which are mounted in a similar manner to the pumps illustrated in FIGS. 3 to 5. In some cases, ten or more pump units may be installed, depending on the size of the pumping mechanism. Gauge 32 allows a mother to monitor the suction pressure and vacuum regulator 34 allows a user to adjust the suction to a desired comfort level.

The breast pump apparatus illustrated in FIGS. 1 to 4 may be used by a mother sitting in the chair, who may use her trunk and thigh muscles to activate the chair in a back and forth motion. The motion is transmitted to the chair movement linkage so as to reciprocate the installed pumps. A lever arrangement may increase the stroke power to a greater than 1:1 ratio. The strong trunk and thigh muscles of the body are able to pump for relatively long periods without tiring, for example fifteen to thirty minutes, in contrast to prior art pumps using hand or foot action with associated smaller muscles which tire more quickly than the larger muscles of the body.

It will be understood that FIGS. 1, 3 and 4 illustrate one possible chair movement mechanism to which the suction pump or multiple pumps 14 may be linked to be driven by the chair's back and forth motion, and that the piston and cylinder may be similarly secured between other relatively movable portions in other chair movement mechanisms in alternative embodiments. The piston and cylinder may be associated with different types of movable seats or user supports, including various different types of chairs such as arm chairs, rocking chairs, reclining chairs, and office chairs, as well as moving benches, sofas, and ottomans in alternative arrangements. In a reclining chair, for example, the pump parts could be connected between the two moving portions of the chair and pumping action could be achieved by a repetitive reclining or up and down motion. The pump could be secured between relatively movable parts of a movement mechanism of any type of movable chair or other moving user support.

The chair powered breast pump apparatus described above makes pumping of milk easier and more efficient by incorporating one or more pump units between relatively moveable parts of the moving mechanism of a movable chair and connecting the suction line or lines to one or more breast shield assemblies via a control panel conveniently mounted on the chair. The chair movement may be a swinging or gliding movement in one or multiple planes, or a reclining movement, so that the mother can power the pump units simply by rocking the chair back and forth and/or up and down, using the larger muscles of the body while the mother is comfortably seated. This has advantages over manually or foot operated breast pumps, which are harder and more tiring to use.

In the foregoing embodiments, the chair operated pump apparatus provides suction to one or more breast shields in a breast pump configuration. However, the pump apparatus may alternatively be configured to perform other pumping tasks in alternative embodiments, such as inflating items such as balloons or air beds simply by operating a movable chair using the larger muscles of the body.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A chair powered breast pump apparatus, comprising:
at least one breast shield assembly having a breast shield adapted to fit over a nipple of a breast and a suction inlet communicating with the breast shield;
at least one pump having a stationary portion and a reciprocating portion for producing reciprocating movement between extended and refracted positions so as to create reduced pressure in an interior of the stationary portion;
a connecting passageway connecting the suction inlet of the breast shield assembly to the stationary portion, whereby suction is applied to the breast shield;
a first connecting bracket configured to connect the reciprocating portion to a first portion of a chair movement mechanism; and
a second connecting bracket configured to secure the stationary portion to a second portion of the chair movement mechanism, the first and second portions being relatively movable during movement of a movable portion of the chair, whereby the reciprocating portion is reciprocated back and forth relative to the stationary portion in successive suction strokes to apply suction to the breast shield.

2. The apparatus of claim 1, wherein the connecting passageway comprises at least one flexible suction line.

3. The apparatus of claim 2, wherein the connecting passageway comprises a first suction line connected to the suction inlet of the breast shield assembly, a second suction line connected to the stationary portion, and a connecting manifold connecting the first suction line to the second suction line.

4. The apparatus of claim 3, further comprising a switch on the connecting manifold for controlling connection of the at least one pump to the breast shield assembly.

5. The apparatus of claim 3, further comprising a second breast shield assembly and an additional first suction line connected to the second breast shield assembly, the connecting manifold having first and second suction ports which are both connected to the second suction line via the connecting manifold, and the additional first suction line being connected to the second suction port.

6. The apparatus of claim 1, further comprising a second pump having a first connecting bracket to secure the reciprocating portion to the first portion of a chair movement mechanism and a second connecting bracket to secure the stationary portion to the second portion of the chair movement mechanism.

7. The apparatus of claim 6, wherein the connecting passageway comprises a connecting manifold having at least one suction port, a first suction line between the suction port and the suction inlet of the breast shield assembly, and a pair of second suction lines between the respective reciprocating portions and the connecting manifold.

8. The apparatus of claim 7, further comprising a manually operable switch which controls communication between the second suction lines and the connecting manifold, whereby one or both pumps may be selectively connected to the suction port.

9. The apparatus of claim 8, wherein the connecting manifold and manually operable switch are disposed within a control panel.

10. The apparatus of claim 9, wherein the chair has an armrest and the control panel is disposed on or in the armrest.

11. The apparatus of claim 9, wherein the control panel is mounted on a moveable tray or table attached to the chair.

12. The apparatus of claim 7, further comprising a second breast shield assembly, the connecting manifold having a second suction port, and a pair of first suction lines connecting the respective breast shield assemblies to the first and second suction port, respectively.

13. The apparatus of claim 1, wherein the pump comprises a piston pump, wherein the reciprocating portion comprises a piston and the stationary portion comprises a cylinder.

14. The apparatus of claim 1, wherein the pump comprises a diaphragm pump, wherein the reciprocating portion comprises a diaphragm and the stationary portion comprises a pump chamber.

15. The apparatus of claim 1, wherein the pump comprises a bellows pump.

16. The apparatus of claim 1, further comprising a pressure gauge which communicates with the connecting passageway to monitor suction pressure.

17. The apparatus of claim 1, further comprising a manually operable pressure regulator in communication with the connecting passageway to control suction pressure applied to the breast shield assembly.

18. A seat and breast pump apparatus, comprising:
- a seat having a base and a user support which is configured to support a user in a seated or prone position;
- a movable linkage mechanism having a first portion secured to the base of the seat and a second portion movable relative to the first portion and secured to the user support of the seat, whereby a user positioned on the user support can move the user support relative to the base;
- at least one pump having a stationary portion and a reciprocating portion connected to the stationary portion for reciprocating movement between extended and retracted positions so as to create reduced pressure in an interior of the stationary portion;
- a first connecting bracket securing the reciprocating portion to one portion of the linkage mechanism and a second connecting bracket securing the stationary portion to the other portion of the linkage mechanism, whereby the reciprocating portion is reciprocated back and forth relative to the stationary portion in successive suction strokes as a user moves the user support relative to the base;
- at least one breast shield assembly having a breast shield adapted to fit over a nipple of a breast, a suction inlet communicating with the breast shield, and a milk outlet configured for connection to a milk container; and
- a connecting passageway connecting the suction inlet to the stationary portion, whereby suction is applied to the breast shield.

19. The apparatus of claim 18, wherein the seat is a rocking chair and the linkage mechanism comprises a pivotal glider linkage.

20. The apparatus of claim 18, wherein the seat is a reclining chair and the linkage mechanism comprises a recliner linkage.

21. The apparatus of claim 18, wherein the seat is an ottoman and the support is configured to support a user's body or legs.

22. The apparatus of claim 18, including at least one additional pump secured between the first and second portions of the linkage mechanism.

23. The apparatus of claim 18, including a plurality of additional pumps secured between the first and second portions of the linkage mechanism.

24. The apparatus of claim 18, wherein the connecting passageway comprises a connecting manifold having at least one suction port, a first suction line connecting the suction port to the suction inlet of the breast shield assembly and a pair of second suction lines connecting the respective piston pumps to the connecting manifold.

25. The apparatus of claim 24, further comprising an additional breast shield assembly, the connecting manifold having first and second suction ports, the first suction line connecting the first suction port to said at least one breast shield assembly, and an additional first suction line connecting the second suction port to said additional breast shield assembly.

26. The apparatus of claim 24, further comprising a switch associated with the manifold which selectively connects one or both of the second suction lines to the manifold, whereby suction from one or both pumps is selectively applied to the breast shield assembly.

27. The apparatus of claim 24, further comprising a control panel associated with the connecting manifold, the seat having at least one arm and the control panel being mounted on the arm, the switch comprising a manually operable switch located on the control panel for operation by the user.

28. The apparatus of claim 27, wherein the control panel is mounted on a moveable tray or table attached to the chair.

29. The apparatus of claim 24, further comprising a pressure regulator associated with the manifold for controlling the suction pressure applied at the suction port.

30. The apparatus of claim 24, further comprising a pressure gauge associated with the manifold for displaying the suction pressure applied at the suction port.

31. The apparatus of claim 18, wherein the pump comprises a piston pump, wherein the reciprocating portion comprises a piston and the stationary portion comprises a cylinder.

32. The apparatus of claim 18, wherein the pump comprises a diaphragm pump, wherein the reciprocating portion comprises a diaphragm and the stationary portion comprises a pump chamber.

33. The apparatus of claim 18, wherein the pump comprises a bellows pump.

* * * * *